United States Patent
Ito et al.

(10) Patent No.: US 6,525,207 B1
(45) Date of Patent: Feb. 25, 2003

(54) PROCESS FOR PREPARING EPOXY COMPOUNDS, AROMATIC COMPOSITIONS CONTAINING THE SAME

(75) Inventors: Nobuhiko Ito, Chiba (JP); Motoo Higashi, Chiba (JP); Yuki Konno, Chiba (JP); Hideaki Takaoka, Chiba (JP)

(73) Assignee: Soda Aromatic Co., Ltd. (JP)

( * ) Notice: Subject to any disclaimer, the term of this patent is extended or adjusted under 35 U.S.C. 154(b) by 0 days.

(21) Appl. No.: 10/110,794

(22) PCT Filed: Sep. 4, 2000

(86) PCT No.: PCT/JP00/05987

§ 371 (c)(1),
(2), (4) Date: Apr. 17, 2002

(87) PCT Pub. No.: WO02/20504

PCT Pub. Date: Mar. 14, 2002

(51) Int. Cl.$^7$ .................. C07D 303/06; C07D 301/26; A61K 7/46; A61K 31/336
(52) U.S. Cl. ................. 549/520; 549/546; 514/475; 512/13
(58) Field of Search ................ 549/520, 546; 514/475; 512/13

(56) References Cited

U.S. PATENT DOCUMENTS 3,287,405 A * 11/1966 Morway et al. ............ 508/506
4,766,107 A * 8/1988 Eberle et al. ................ 512/13

* cited by examiner

Primary Examiner—Ba K. Trinh
(74) Attorney, Agent, or Firm—Schnader Harrison Segal & Lewis LLP

(57) ABSTRACT

This invention provides a process for producing an epoxy compound industrially advantageously at low cost in a short process. Furthermore, this invention provides a novel fruity, camphoric, floral, amber or woody fragrance-, flavor- or scent-imparting composition containing said epoxy compound, and foods & drinks, perfumes, cosmetics and tobaccos containing said composition.

The epoxy compound can be produced by letting an α-halocyclododecanone and an organic magnesium compound react with each other for Grignard reaction, hydrolyzing to obtain a halohydrin and letting the halohydrin and a base react with each other in the presence of an phase transfer catalyst or adding an aprotic polar solvent for reaction.

12 Claims, No Drawings

PROCESS FOR PREPARING EPOXY COMPOUNDS, AROMATIC COMPOSITIONS CONTAINING THE SAME

This application is a 371 of PCT/JP00/05987 dated Sep. 4, 2000.

TECHNICAL FIELD

This invention relates to a process for producing an epoxy compound represented by the following general formula (4):

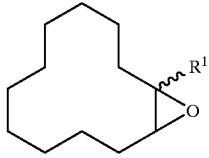

(4)

(where $R^1$ denotes an alkyl group with 1 to 5 carbon atoms, alkenyl group with 2 to 5 carbon atoms or alkynyl group with 2 to 5 carbon atoms, and the wavy line denotes cis form, trans form or a mixture consisting of cis form and trans form.)

This invention also relates to a fragrance-, flavor- or scent-imparting composition containing said epoxy compound, and also to drinks & foods, perfumes, cosmetics and tobaccos respectively containing said compound.

The novel fragrance-, flavor- or scent-imparting composition containing said epoxy compound and foods & drinks, perfumes, cosmetics and tobaccos respectively containing said composition are intensified in fruity, camphoric, floral, amber or woody fragrance, flavor or scent.

BACKGROUND ART

Among the compounds represented by the general formula (4), 1-vinyl-13-oxabicyclo[10.1.0]tridecane is a publicly known chemical substance, and it is a useful compound for producing 5-cyclohexadecenone. The method of using the epoxy compound is described in JP 49-47345, A Gazette.

However, the fragrant properties of these epoxy compounds have not been recognized so far. Of course, there is no report about the use of them as fragrance-, flavor- or scent-imparting compositions and foods & drinks, perfumes, cosmetics and tobaccos respectively containing said compositions.

It is only known that 1,5,9-trimethyl-13-oxabicyclo[10.1.0]trideca-4,8-diene as an epoxy compound similar to the epoxy compounds represented by the general formula (4) has a woody amber fragrance.

As a method of synthesizing the 1-vinyl-13-oxabicyclo[10.1.0]tridecane, for example, disclosed is a process comprising the steps of letting vinylmagnesium chloride act on 2-chlorocyclododecanone, to make chlorohydrin, and cyclizing using sodium hydroxide or sodium methoxide as a base, as shown in the following reaction formula ("Synthetic Perfume Chemistry and Knowledge on Commercial Products (in Japanese)", Yukagaku, 1974, Vol. 23, No. 6, Page 371). However, it does not describe anything at all about the stereochemistry of the obtained product.

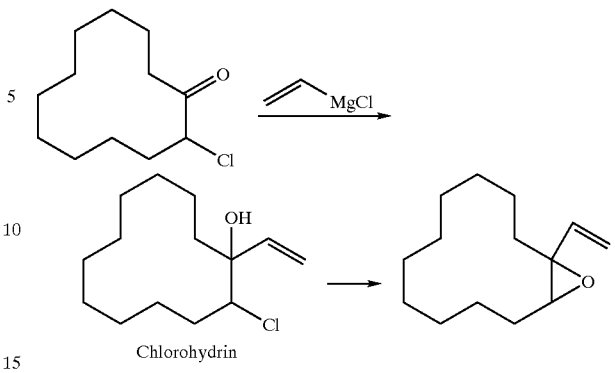

Chlorohydrin

However, the process for producing said epoxy compound has the following problem: the solvent must be once recovered after production of chlorohydrin, to increase the number of production steps; the cyclization reaction using sodium hydroxide as a base requires a long time and is low in yield; and sodium methoxide is relatively expensive and the treatment of the waste liquid after completion is difficult industrially disadvantageously.

On the other hand, it is general that compounds used as perfumes are quite different in fragrance even if they are slightly different in structure. So, it is very important for obtaining novel fragrances, to synthesize various compounds for examining their fragrances. Furthermore, the materials to be mixed are required to satisfy various demands such as low prices and unique fragrances. Numerous perfume materials that have a fruity, camphoric, floral, amber or woody fragrance are known, but the fashion of fragrances keeps changing with the age. So, it is very important to find novel perfume materials.

An object of this invention is to provide a process for producing an epoxy compound with said performance industrially advantageously at low cost in a short process.

Another object of this invention is to provide a novel fruity, camphoric, floral, amber or woody fragrance-, flavor- or scent-imparting composition, and foods & drinks, perfumes, cosmetics and tobaccos respectively containing said composition.

DISCLOSURE OF THE INVENTION

The inventors studied intensively to solve the problems of the conventional methods as described above, and found that epoxy compounds can be easily produced by means of a specific process. Thus, this invention has been completed.

The first subject matter of this invention is a process for producing an epoxy compound represented by the following general formula (4)

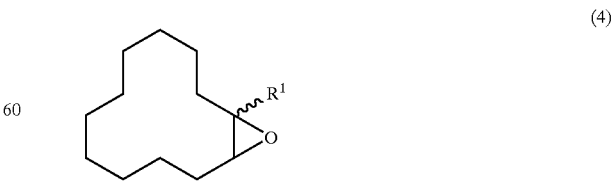

(4)

(where $R^1$ denotes an alkyl group with 1 to 5 carbon atoms, alkenyl group with 2 to 5 carbon atoms or alkynyl group with 2 to 5 carbon atoms, and the wavy line denotes cis form, trans form or a mixture consisting of cis form and transform), comprising the steps of letting an α-halocyclododecanone represented by the following general formula (1)

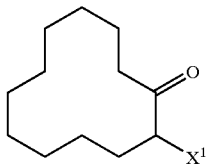
(1)

(where $X^1$ denotes chlorine, bromine or iodine) and an organic magnesium compound represented by the following general formula (2)

$R^1MgX^1$ (2)

(where $R^1$ denotes an alkyl group with 1 to 5 carbon atoms, alkenyl group with 2 to 5 carbon atoms or alkynyl group with 2 to 5 carbon atoms, and $X^1$ denotes chlorine, bromine or iodine) react with each other for Grignard reaction, hydrolyzing to obtain a halohydrin represented by the following general formula (3)

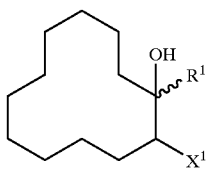
(3)

(where $R^1$ denotes an alkyl group with 1 to 5 carbon atoms, alkenyl group with 2 to 5 carbon atoms or alkynyl group with 2 to 5 carbon atoms; $X^1$ denotes chlorine, bromine or iodine; and the wavy line denotes cis form, trans form or a mixture consisting of cis form and trans form), and letting the halohydrin and a base react with each other in the presence of an phase transfer catalyst.

The second subject matter of this invention is a process for producing a compound represented by said general formula (4), comprising the steps of letting an α-halocyclododecanone represented by the following general formula (1)

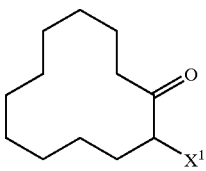
(1)

(where $X^1$ denotes chlorine, bromine or iodine) and an organic magnesium compound represented by the following general formula (2)

$R^1MgX^1$ (2)

(where $R^1$ denotes an alkyl group with 1 to 5 carbon atoms, alkenyl group with 2 to 5 carbon atoms or alkynyl group with 2 to 5 carbon atoms, and $X^1$ denotes chlorine, bromine or iodine) react with each other for Grignard reaction, and adding an aprotic polar solvent, for epoxidation.

The third subject matter of this invention is a novel fruity, camphoric, floral, amber or woody fragrance-, flavor- or scent-imparting composition containing an epoxy compound represented by said general formula (4), and foods & drinks, perfumes, cosmetics and tobaccos respectively containing said composition.

THE BEST MODES FOR CARRYING OUT THE INVENTION

At first, an epoxy compound represented by said general formula (4) can be synthesized according to either of the following two processes.

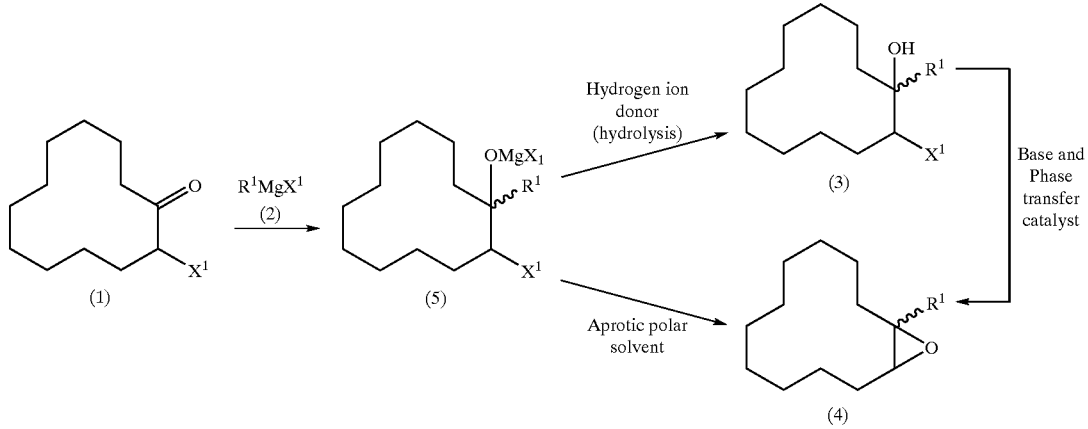

(where $R^1$ denotes an alkyl group with 1 to 5 carbon atoms, alkenyl group with 2 to 5 carbon atoms or alkynyl group with 2 to 5 carbon atoms, and the wavy line denotes cis form, trans form or a mixture consisting of cis form and trans form).

In the first synthesizing process, an α-haloketone represented by the formula (1) and an organic magnesium compound represented by the formula (2) are made to react with each other for Graignard reaction, to produce an alkoxymagnesium halide represented by the formula (5), and a hydrogen ion donor is added for hydrolysis, to produce chlorohydrin represented by the formula (3). Then, a base is caused to act on it in the presence of an phase transfer catalyst, for epoxidation reaction, to form an epoxy compound represented by the formula (4).

In the second process, an α-haloketone represented by the formula (1) and an organic magnesium compound represented by the formula (2) are made to react with each other for Grignard reaction, to produce an alkoxymagnesium halide represented by the formula (5), and an aprotic polar solvent is added for cyclization reaction, to form an epoxy compound represented by the formula (4).

In the organic magnesium compound represented by the formula (2), $R^1$ denotes an alkyl group with 1 to 5 carbon atoms, alkenyl group with 2 to 5 carbon atoms or alkynyl group with 2 to 5 carbon atoms. Alkyl groups with 1 to 5 carbon atoms include a methyl group, ethyl group, propyl group, isopropyl group, butyl group, t-butyl group, 1-methylpropyl group, 2-methylpropyl group, pentyl group, 1,2-diemthylpropyl group, 1,1-dimethylpropyl group, 2,2-dimethylpropyl group, etc., though not limited thereto in this invention. Alkenyl groups with 2 to 5 carbon atoms include a vinyl group, 1-propenyl group, 1-butenyl group, 2-butenyl group, 3-butenyl group, 1-pentenyl group, 2-pentenyl group, 3-pentenyl group, 4-pentenyl group, 2-methylpropenyl group, allyl group, 1,1-dimethylallyl group, etc., though not limited thereto in this invention. Alkynyl groups with 2 to 5 carbon atoms include an ethynyl group, 1-propynyl group, 2-propynyl group, 1-butynyl group, 2-butynyl group, 3-butynyl group, 1-pentynyl group, 2-pentynyl group, 3-pentynyl group and 4-pentynyl group, though not limited thereto in this invention. $X^1$ denotes a halogen atom such as a chlorine atom, bromine atom or iodine atom.

The amount of the organic magnesium compound used in this invention is one equivalent or more for each equivalent of the substrate, and a preferable range is 1.1 to 3.0 equivalents.

The solvents that can be used in the Grignard reaction between the α-haloketone represented by the formula (1) and the organic magnesium compound represented by the formula (2) include ether compounds such as diethyl ether and tetrahydrofuran, aliphatic hydrocarbon compounds such as petroleum ether and cyclohexane, aromatic compounds such as benzene, toluene and xylene, and halogen compounds such as chloroform, dichloromethane and dichloroethane.

These solvents can also be used as a mixture obtained by mixing them at a desired ratio. Among them, tetrahydrofuran and toluene are especially preferable. The used amount of the solvent is usually 100 to 5000 wt %, preferably 500 to 2000 wt % based on the weight of the substrate.

It is preferable that the reaction temperature of the Grignard reaction between the α-haloketone represented by the formula (1) and the organic magnesium compound represented by the formula (2) is −20 to 30° C. A more preferable range is 0 to 20° C. It is preferable that the reaction time is 0.5 to 3 hours. A more preferable range is 1 to 2 hours.

The hydrogen ion donors that can be used for hydrolyzing the alkoxymagnesium halide represented by the formula (5) include water, mineral acid aqueous solutions such as hydrochloric acid aqueous solution and sulfuric acid aqueous solution, organic acid aqueous solutions such as formic acid aqueous solution, oxalic acid aqueous solution and acetic acid aqueous solution, ammonium chloride aqueous solution, etc. Among them, hydrochloric acid aqueous solution is especially preferable.

After the alkoxymagnesium halide is hydrolyzed, the solution is separated to take out the organic layer, and the organic layer is preferably washed with an alkali and used for the subsequent epoxidation reaction.

The phase transfer catalysts that can be used in this invention include phosphonium, sulfonium and ammonium compounds. Preferably ammonium compounds can be used and they can be represented by the following general formula (6).

(where $R^2$ to $R^5$ denote, respectively independently, an alkyl group with 1 to 11 carbon atoms or benzyl group, and $X^2$ denotes a iodide, bromide, chloride, hydroxide or hydrogensulfate). The ammonium compounds include, for example, tetramethylammonium chloride, tetraethylammonium chloride, tetrapropylammonium chloride, tetrabutylammonium chloride, tetramethylammonium bromide, tetraethylammonium bromide, tetrapropylammonium bromide, tetrabutylammonium bromide, tetrabutylammonium iodide, benzyltrimethylammonium chloride, benzyltrimethylammoniumbromide, benzyltriethylammonium chloride, benzyltriethylammonium bromide, benzyltributylammonium chloride, benzyltributylammonium bromide, trioctylmethylammonium chloride, tetrabutylammonium hydrogensulfate, tetrabutylammonium hydroxide, etc. As the phase transfer catalyst, a polymer support ammonium compound can also be used.

The used amount of the phase transfer catalyst can be 0.01 mol % or more based on the amount of the substrate. A preferable range is 0.1 to 30 mol %.

The bases that can be used in the cyclization reaction of the chlorohydrin represented by the formula (3) include alkali metal hydroxides and alkali metal carbonates. Preferable are sodium hydroxide, potassiumhydroxide, lithiumhydroxide, sodiumcarbonate, potassium carbonate and lithium carbonate. The used amount of the base can be 1 equivalent or more for each equivalent of the substrate, though depending on the reacting substrate. A preferable range is 2 to 5 equivalents. The base is usually used as an aqueous solution. A higher base concentration is more advantageous for the reaction. A preferable concentration range is 5 to 50%. The used amount of the base aqueous solution is usually 100 to 5000 wt % based on the weight of the substrate. A preferable range is 300 to 2000 wt %.

In the cyclization reaction of chlorohydrin represented by the formula (3), it is preferable that the reaction temperature is 0 to 120°. A more preferable range is 80 to 110° C. Furthermore, it is preferable that the reaction time is 1 to 24 hours. A more preferable range is 2 to 12 hours.

The aprotic polar solvents that can be added to the alkoxymagnesium halide represented by the formula (5) produced by the Grignard reaction between the α-haloketone represented by the formula (1) and the organic magnesium compound represented by the formula (2) include N,N'-dimethylpropyleneurea (DMPU), 1,3-dimethyl-2-imidazolidinone (DMI), hexamethylphosphoric acid triamide (HMPA), DMSO, DMF, 1,1,3,3-tetramethylurea (TMU), 1-methyl-2-pyrrolidinone (NMP), etc. In view of reactivity, safety, price, etc., DMPU and DMI can be especially preferably used. It is preferable that the added amount of the aprotic polar solvent is 2 to 10 equivalents for each equivalent of the organic magnesium compound. A more preferable range is 3 to 5 equivalents.

It is preferable that the reaction temperature after adding the aprotic polar solvent is 20 to 100° C. A more preferable range is 40 to 80° C. Furthermore, it is preferable that the reaction time is 30 minutes to 24 hours. A more preferable range is 1 to 12 hours.

As the epoxy compound represented by said general formula (3) obtained in this invention, two isomers of cis form and trans form attributable to epoxy groups exist, and both the isomers can be used at a desired ratio from 0 to 100 respectively. The epoxy compound has a very strong and sustainable fruity, camphoric, floral, amber or woody fragrance. Especially 1-vinyl-13-oxabicyclo[10.1.0]tridecane which is an epoxy compound having a vinyl group as $R^1$ of the general formula (3) has a very strong amber scent, and its cis isomer has a very diffusive woody, amber and sandalwood-like fragrance. On the other hand, the trans isomer has a strong woody animal scent.

The epoxy compound obtained in this invention can be used as a fragrance-, flavor- or scent-imparting composition (flavor and fragrance composition) singly or as a mixture with another ingredient such as a perfume. The flavor and fragrance composition can be added to foods & drinks, perfumes, cosmetics and tobaccos. The perfume composition can contain any ingredient used in ordinary perfumes without any restriction.

When the epoxy compound of this invention is used to produce a flavor and fragrance composition, the added amount can be selected usually in a range of 0.01 to 30 parts by weight, but depending on the intended sensory effect, an amount outside this range can also be used.

Furthermore, the epoxy compound obtained in this invention can be added as a fragrance-, flavor- or scent-imparting flavor and fragrance composition to various foods & drinks, perfumes, cosmetics and tobaccos, for giving the fragrance, flavor to scent peculiar to the epoxy compound. The amount of the epoxy compound of this invention added to various foods & drinks, perfumes, cosmetics and tobaccos can be adequately selected depending on the kinds of the foods & drinks, perfumes, cosmetics and tobaccos to which it is added.

The fragrance-, flavor- or scent-imparting perfume composition containing the epoxy compound of this invention can be added without any particular restriction to any various foods & drinks, perfumes, cosmetics and tobaccos desired to be given the fragrance-, flavor- or scent-imparting effect of the perfume composition. For example, it can be used for giving a fragrance to a wide range of products such as soaps, shampoos, cosmetics, sprays, aromatics, deodorants, washing agents and textile softeners, and also for producing base materials of perfumes. Furthermore, it can be added to strongly carbonated, weakly carbonated or non-carbonated beverages such as fruit drinks, fruit wine and milk drinks, ices such as ice creams and sherbets, Japanese and Western confectionaries, favorite foods such as jams, chewing gums, tea, coffee, cocoa and green tea, other food additives, animal feeds, etc.

For tobaccos, it can be added to cigarettes, pipe tobaccos and cigars respectively produced from ordinary leaf tobaccos, and synthetic tobaccos produced using natural fibers or tissue-cultured plants. In the case of cigarettes, even if it is added to the materials used for producing tobaccos such as paper, glue, filters and the like, the intended scent-imparting effect can be obtained. Other applications include various health and sanitation materials such as disinfectants, and taste improvers and flavors to facilitate the administration of drugs.

Examples

This invention is described below particularly in reference to examples, but is not limited thereto or thereby.

Example 1

Synthesis of 1-vinyl-13-oxabicyclo[13.1.0]tridecane

A four-neck flask equipped with a thermometer, stirrer and condenser tube was charged with a tetrahydrofuran solution of vinylmagnesium (1.31 mol), and toluene (600 ml) was added to the solution. At 0° C., a toluene solution of 2-chlorocyclododecanone (159 g, 0.735 mol) was added dropwise to the solution, for reaction for 1 hour. After completion of reaction, 16% hydrochloric acid (120 g) was added for hydrolysis, and the solution was separated to take out the organic layer. The organic layer was washed with 2% sodium hydroxide aqueous solution (320 ml). To the obtained toluene solution, added were 30% sodium hydroxide aqueous solution (370 g, 2.78 mol) and benzyltriethylammonium chloride (1.86 g 0.00816 mol), and the mixture was stirred for reaction at 95° C. for 6 hours. After completion of reaction, the solution was separated to take out the organic layer, and the organic layer was washed with a saline solution. The solvent was distilled away under reduced pressure, and the residue was distilled for purification under reduced pressure, to obtain 133 g of a distillate. It was analyzed by means of capillary gas chromatography and found to be a mixture containing 61% of cis-1-vinyl-13-oxabicyclo[10.1.0]tridecane and 37% of trans-1-vinyl-13-oxabicyclo[10.1.0]tridecane (yield was 85%). The distillate was partially separated by means of silica gel chromatography for isolation into trans-1-vinyl-13-oxabicyclo[10.1.0]tridecane and cis-1-vinyl-13-oxabicyclo[10.1.0]tridecane.

Trans-1-vinyl-13-oxabicyclo[10.1.0]tridecane

NMR(1H, 500 MHz, CDCl$_3$) δ ppm 1.24–1.65(18H, m), 1.74–1.87(2H, m), 2.79(1H, m), 5.16(1H, dd, J=1.5, 11 Hz), 5.32(1H, dd, J=1.5, 17 Hz) 5.98(1H, dd, J=11, 17 HZ)

IR(vmax)cm$^{-1}$ 2949, 1638,1412 987, 928

MS 208(M$^+$, 9) 165(16), 123(16), 95(55), 83(64), 67(70), 55(100), 41(74)

Cis-1-vinyl-13-oxabicyclo[10.1.0]tridecane

NMR(1H, 500 MHz, CDCl$_3$) δ ppm 1.17–1.63(18H, m), 1.92(1H, m), 2.26(1H, ddd, J=3, 6.5, 13.5 Hz) 3.10(1H, dd, J=3, 10 Hz), 5.31(1H, dd, J=1.5, 11 Hz), 5.33(1H, dd, J=1.5, 17 Hz) 5.99(1H, dd, J=11, 17 Hz)

IR(vmax)cm$^{-1}$ 2949, 1638,1454 989, 934

MS 208(M$^+$, 9) 165(16), 123(16), 95(57), 83(67), 67(72), 55(100), 41(72)

Example 2

Synthesis of 1-vinyl-13-oxabicyclo[13.1.0]tridecane

A four-neck flask equipped with a thermometer, stirrer and condenser tube was charged with a tetrahydrofuran solution of vinylmagnesium (24 mmol), and to the solution, toluene (16 ml) was added. At 0° C., a toluene solution of 2-chlorocyclododecanone (2.93 g, 13.5 mol) was added dropwise for reaction for 1 hour. After completion of reaction, 16% hydrochloric acid (5 g) was for hydrolysis, and the solution was separated to take out the organic layer. The organic layer was washed with 2% sodium hydroxide aqueous solution (10 ml). To the obtained toluene solution, added were 30% sodium hydroxide aqueous solution (6.8 g, 51.0 mmol) and tetrabutylammonium chloride (0.0417 g, 0.150 mmol), and the mixture was stirred for reaction at 95° C. for 2 hours. After completion of reaction, the solution was separated to take out the organic layer, and the organic layer was washed with 10% sulfuric acid (5 ml), saturated sodium hydrogencarbonate aqueous solution (10 ml) and a saline solution (10 ml). The solvent was distilled away under reduced pressure, and the residue was distilled for purification under reduced pressure, to obtain 1-vinyl-13-oxabicyclo

[10.1.0]tridecane (2.44g, 11.5 mmol, chemical purity 98%, cis form:trans form=58:42). The yield was 85%.

Example 3

Synthesis of 1-vinyl-13-oxabicyclo[13.1.0]tridecane

A four-neck flask equipped with a thermometer, stirrer and condenser tube was charged with a tetrahydrofuran solution of vinylmagnesium (24 mmol), and toluene (16 ml) was added to the solution. At 0° C., a toluene solution of 2-chlorocyclododecanone (2.93 g, 13.5 mmol) was added dropwise for reaction for 1 hour. After completion of reaction, 16% hydrochloric acid (5 g) was added for hydrolysis, and the solution was separated to take out the organic layer. The organic layer was washed with 2% sodium hydroxide aqueous solution (10 ml). To the obtained toluene solution, added were 30% sodium hydroxide aqueous solution (6.8 g, 51.0 mmol) and tetrabutylammonium chloride (0.0417 g, 0.150 mmol), and the mixture was stirred for reaction at 95° C. for 2 hours. After completion of reaction, the solution was separated to take out the organic layer, and the organic layer was washed with 10% sulfuric acid (5 ml), saturated sodium hydrogencarbonate aqueous solution (10 ml) and a saline solution (10 ml). The solvent was distilled away under reduced pressure, and the residue was distilled for purification under reduced pressure, to obtain 1-vinyl-13-oxabicyclo[10.1.0]tridecane (2.44 g, 11.5 mmol, chemical purity 98%, cis form:trans form=59:41). The yield was 85%.

Example 4

Synthesis of 1-vinyl-13-oxabicyclo[13.1.0]tridecane

A four-neck flask equipped with a thermometer, stirrer and condenser tube was charged with a tetrahydrofuran solution of vinylmagnesium (24 mmol), and to the solution, toluene (16 ml) was added. At 0° C., a toluene solution of 2-chlorocyclododecanone (2.94 g, 13.5 mol) was added dropwise for reaction for 1 hour. After completion of reaction, 16% hydrochloric acid (5 g) was added for hydrolysis, and the solution was separated to take out the organic layer. The organic layer was washed with 2% sodium hydroxide aqueous solution (10 ml). To the obtained toluene solution, added were 30% sodium hydroxide aqueous solution (6.8 g, 51.0 mmol) and tetrabutylammonium chloride (0.0417 g, 0.150 mmol), and the mixture was stirred for reaction at 95° C. for 2 hours. After completion of reaction, the solution was separated to take out the organic layer, and the organic layer was washed with 10% sulfuric acid (5 ml), saturated sodium hydrogencarbonate aqueous solution (10 ml) and a saline solution (10 ml). The solvent was distilled away under reduced pressure, and the residue was distilled for purification under reduced pressure, to obtain 1-vinyl-13-oxabicyclo[10.1.0]tridecane (2.42 g, 11.5 mmol, chemical purity 99%, cis form:trans form=86:14). The yield was 85%.

Example 5

Synthesis of 1-vinyl-13-oxabicyclo[10.1.0]tridecane

A four-neck flask equipped with a thermometer, stirrer and condenser tube was charged with 100 g (0.46 mol) of 2-chlorocyclododecanone and 122 g of tetrahydrofuran, and at −10 to 0° C., a THF solution of vinylmagnesium chloride (0.82 mol) was added dropwise. The mixture was allowed to stand for reaction for 30 minutes, and 420 g (3.27 mol) of N,N'-dimethylpropyleneurea (DMPU) was added. The mixture was heated to 50° C. and allowed to stand for reaction for 1 hour, and saturated ammonium chloride aqueous solution was added dropwise for inactivation. The reaction mixture was subjected to extraction with hexane, and the solvent was recovered. The residue was distilled to obtain 1-vinyl-13-oxabicyclo[10.1.0]tridecane (80 g, 0.38 mol, chemical purity 98%, cis form:trans form=88:12). The yield was 82%.

Operations were made as described for Example 5, except that the solvent added was changed as shown in the following table, and the results were as shown in the following table.

| | | Reaction conditions | | | Yield |
|---|---|---|---|---|---|
| | Solvent added | ° C. | Hr | Cis:trans | mol % |
| 1 | DMI | 50 | 4 | 86:14 | 76 |
| 2 | TMU | 50 | 10 | 86:14 | 79 |
| 3 | NMP | 50 | 2 | 87:13 | 81 |

Example 6

Musky Floral Fragrance-imparting Composition

As a musky floral composition, the following ingredients were mixed.

| Ingredient | Parts by weight |
|---|---|
| Cyclohexadecenolide | 4 |
| Bergamot oil | 80 |
| Lemon oil | 2 |
| Heliobouquet | 20 |
| Lily aldehyde | 80 |
| Cyclopentadecanolide | 500 |
| Mint oil | 2 |
| Rose oil | 20 |
| Citronellol | 80 |
| Isobornylcyclohexanol | 200 |
| Basil oil | 2 |
| Total | 990 |

To the mixture composed of the above, 10 parts by weight of 1-vinyl-13-oxabicyclo(10.1.0)tridecane (cis form:trans form=62:38) were added to obtain a novel composition. The addition of 1-vinyl-13-oxabicyclo(10.1.0)tridecane could give a powerful natural woody amber musky scent and emphasize it.

Example 7

Mint Flavor Type Fragrance-, Flavor- and Scent-imparting Composition

The following ingredients were mixed as a mint flavor type composition.

| Ingredient | Parts by weight |
|---|---|
| α-pinene | 5 |
| □-pinene | 15 |
| 1-limonene | 15 |
| β-caryophyllene | 15 |
| 1,8-cineole | 10 |
| 1-menthol | 290 |
| 1-menthone | 110 |

| Ingredient | Parts by weight |
| --- | --- |
| 3-octanol | 10 |
| 1-menthyl acetate | 30 |
| Anise oil | 25 |
| Wintergreen oil | 5 |
| Eucalyptus oil | 45 |
| Coliander oil | 5 |
| Peppermint oil | 400 |
| Total | 980 |

To the mixture consisting of the above ingredients, 20 parts by weight of 1-vinyl-13-oxabicyclo(10.1.0)tridecane (cis form:trans form=88:12) was added to obtain a novel composition. The addition of 1-vinyl-13-oxabicyclo(10.1.0) tridecane could give newly a bodily, sweet and swollen scent.

Industrial Applicability

Since the fragrances of the compounds used for perfumes are quite different even if they are slightly different in structure, it is very important for obtaining novel scents, to synthesize various compounds for examining their fragrances. Furthermore, the materials to be mixed are required to satisfy various demands such as low prices and unique fragrances, and the fashion of fragrances incessantly changes with the age. So, it is very important to find novel perfume materials.

This invention can provide a novel fruity, camphoric, floral, amber or woody fragrance-, flavor- or scent-imparting composition (flavor and fragrance composition) containing an epoxy compound with a specific chemical structure. The foods & drinks, perfumes, cosmetics and tobaccos respectively containing the flavor and fragrance composition are given a novel fruity, camphoric, floral, amber or woody fragrance, flavor or scent.

Furthermore, conventional epoxy compound production methods need many steps of production or long time or are low in yield, or need the treatment of the waste liquid remaining after reaction. However, the process for producing an epoxy compound of this invention allows the epoxy compound with said performance to be produced industrially advantageously at low cost in a short process.

What is claimed is:

1. A process for producing an epoxy compound represented by the following general formula (4)

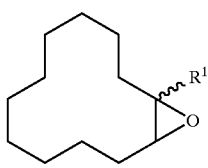

(4)

(where $R^1$ denotes an alkyl group with 1 to 5 carbon atoms, alkenyl group with 2 to 5 carbon atoms or alkynyl group with 2 to 5 carbon atoms, and the wavy line denotes cis form, trans form or a mixture consisting of cis form and transform), comprising the steps of letting an α-halocyclododecanone represented by the following general formula (1)

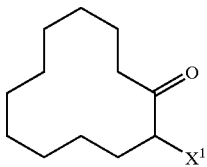

(1)

(where $X^1$ denotes chlorine, bromine or iodine) and an organic magnesium compound represented by the following general formula (2)

$$R^1MgX^1 \quad (2)$$

(where $R^1$ denotes an alkyl group with 1 to 5 carbon atoms, alkenyl group with 2 to 5 carbon atoms or alkynyl group with 2 to 5 carbon atoms, and $X^1$ denotes chlorine, bromine or iodine) react with each other for Grignard reaction, hydrolyzing to obtain a halohydrin represented by the following general formula (3)

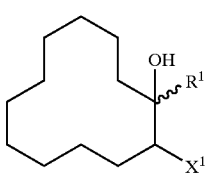

(3)

(where $R^1$ denotes an alkyl group with 1 to 5 carbon atoms, alkenyl group with 2 to 5 carbon atoms or alkynyl group with 2 to 5 carbon atoms; $X^1$ denotes chlorine, bromine or iodine; and the wavy line denotes cis form, trans form or a mixture consisting of cis form and trans form), and letting the halohydrin and a base react with each other in the presence of an phase transfer catalyst.

2. A process for producing an epoxy compound, comprising the steps of letting an α-halocyclododecanone represented by the following general formula (1)

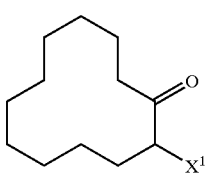

(1)

(where $X^1$ denotes chlorine, bromine or iodine) and an organic magnesium compound represented by the following general formula (2)

$$R^1MgX^1 \quad (2)$$

(where $R^1$ denotes an alkyl group with 1 to 5 carbon atoms, alkenyl group with 2 to 5 carbon atoms or alkynyl group with 2 to 5 carbon atoms, and $X^1$ denotes chlorine, bromine or iodine) react with each other for Grignard reaction, and adding an aprotic polar solvent, for epoxidation.

3. A process for producing an epoxy compound, according to claim 1 or 2, wherein the $X^1$ in the general formula (1) denotes chlorine.

4. A process for producing an epoxy compound, according to claim 1 or 2, wherein the $X^1$ in the general formula (2) denotes chlorine or bromine.

5. A process for producing an epoxy compound, according to any one of claims 1 through 4, wherein the $R^1$ in the general formula (4) denotes a methyl group, ethyl group, propyl group, butyl group, vinyl group, allyl group or 1,1-dimethylallyl group.

6. A process for producing an epoxy compound, according to any one of claims 1 through 4, wherein the $R^1$ in the general formula (4) denotes a vinyl group.

7. A process for producing an epoxy compound, according to any one of claims 1 and 3 through 6, wherein the phase transfer catalyst is benzyltriethylammonium chloride, tetrabutylammonium bromide, tetrabutylammoniumhydrogensulfate, tetrabutylammoniumchloride or tetrabutylammonium hydroxide.

8. A process for producing an epoxy compound, according to any one of claims 1 and 3 through 7, wherein the base is sodium hydroxide, potassium hydroxide, sodium carbonate or potassium carbonate.

9. A process for producing an epoxy compound, according to any one of claims 2 through 6, wherein the aprotic polar solvent is N,N'-dimethylpropyleneurea (DMPU), 1,3-dimethyl-2-imidazolidinone (DMI), 1,1,3,3-tetramethylurea (TMU) or 1-methyl-2-pyrrolidinone (NMP).

10. A fragrance-, flavor- or scent-imparting composition, comprising an epoxy compound represented by the following general formula (4)

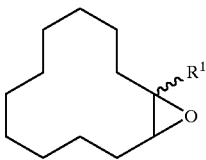

(4)

(where $R^1$ denotes an alkyl group with 1 to 5 carbon atoms, alkenyl group with 2 to 5 carbon atoms or alkynyl group with 2 to 5 carbon atoms, and the wavy line denotes cis form, trans form or a mixture consisting of cis form and trans form).

11. A fragrance-, flavor- or scent-imparting composition, according to claim 10, wherein the $R^1$ in the general formula (4) denotes a methyl group, ethyl group, propyl group, butyl group, vinyl group, allyl group or 1,1-dimethylallyl group.

12. A fragrance-, flavor- or scent-imparting composition, according to claim 10, wherein the $R^1$ in the general formula (4) denotes a vinyl group.

* * * * *